United States Patent
Hudgins et al.

(10) Patent No.: US 7,534,268 B2
(45) Date of Patent: May 19, 2009

(54) DEVICES AND METHODS FOR DISC REPLACEMENT

(75) Inventors: Robert Garryl Hudgins, Burnsville, MN (US); Bruce Robie, Glen Rock, NJ (US)

(73) Assignee: Zimmer Spine, Inc., Minneapolis, MN (US)

( * ) Notice: Subject to any disclaimer, the term of this patent is extended or adjusted under 35 U.S.C. 154(b) by 178 days.

(21) Appl. No.: 11/385,488

(22) Filed: Mar. 20, 2006

(65) Prior Publication Data
US 2007/0168042 A1 Jul. 19, 2007

Related U.S. Application Data

(63) Continuation of application No. 11/332,622, filed on Jan. 13, 2006.

(51) Int. Cl.
*A61F 2/44* (2006.01)
(52) U.S. Cl. .................. 623/17.12; 623/17.11; 606/279
(58) Field of Classification Search .................. 606/61, 606/246, 279; 623/17.11–17.16
See application file for complete search history.

(56) References Cited

U.S. PATENT DOCUMENTS

| | | | |
|---|---|---|---|
| 5,047,055 A | 9/1991 | Bao et al. | |
| 5,192,326 A | 3/1993 | Bao et al. | |
| 5,534,028 A | 7/1996 | Bao et al. | |
| 5,549,679 A | 8/1996 | Kuslich | |
| 5,571,189 A | 11/1996 | Kuslich | |
| 5,702,454 A * | 12/1997 | Baumgartner | 128/898 |
| 5,824,093 A | 10/1998 | Ray et al. | |
| 5,976,186 A | 11/1999 | Bao et al. | |
| 6,187,048 B1 | 2/2001 | Milner et al. | |
| 6,280,475 B1 | 8/2001 | Bao et al. | |
| 6,332,894 B1 | 12/2001 | Stalcup et al. | |
| 6,375,682 B1 | 4/2002 | Fleischmann et al. | |
| 6,402,784 B1 | 6/2002 | Wardlaw | |

(Continued)

FOREIGN PATENT DOCUMENTS

WO 2004089257 A1 10/2004

OTHER PUBLICATIONS

European Patent Office, Search Report and Written Opinion received in corresponding PCT Application No. PCT/US2007/060457, dated Oct. 12, 2007, 17 pgs.

(Continued)

*Primary Examiner*—Eduardo C Robert
*Assistant Examiner*—Andrew Yang
(74) *Attorney, Agent, or Firm*—Crompton, Seager & Tufte, LLC.

(57) ABSTRACT

The present disclosure concerns implants to at least partially replace the nucleus of a spinal disc. In one embodiment, a prosthetic implant is provided which includes a bag structure having a fixation component or member, the bag operable to contain at least one internal implant within the bag. In other embodiments, a bag structure is provided with a flange adaptable to anchor the structure to a vertebral body and a sinusoidal-shaped structure made of a flexible material is provided with various unique configurations. In one embodiment, for delivery, a bag structure with a flange may be attached to a vertebral body. In another embodiment, a sinusoidal-shaped implant structure is alternately woven from one end to the other with a second sinusoidal-shaped structure.

15 Claims, 7 Drawing Sheets

U.S. PATENT DOCUMENTS

| | | | |
|---|---|---|---|
| 6,419,704 B1 * | 7/2002 | Ferree | 623/17.12 |
| 6,425,923 B1 | 7/2002 | Stalcup et al. | |
| 6,443,988 B2 | 9/2002 | Felt et al. | |
| 6,447,543 B1 | 9/2002 | Studer et al. | |
| 6,620,196 B1 | 9/2003 | Trieu | |
| 6,645,248 B2 | 11/2003 | Casutt | |
| 6,712,853 B2 | 3/2004 | Kuslich | |
| 6,733,533 B1 | 5/2004 | Lozier | |
| 7,001,431 B2 * | 2/2006 | Bao et al. | 623/17.12 |
| 2002/0026244 A1 | 2/2002 | Trieu | |
| 2002/0068974 A1 | 6/2002 | Kuslich et al. | |
| 2003/0033017 A1 | 2/2003 | Lotz et al. | |
| 2003/0220649 A1 | 11/2003 | Bao et al. | |
| 2004/0220669 A1 | 11/2004 | Studer | |
| 2004/0225361 A1 * | 11/2004 | Glenn et al. | 623/17.12 |
| 2005/0090901 A1 | 4/2005 | Studer | |
| 2005/0143827 A1 * | 6/2005 | Globerman et al. | 623/17.16 |
| 2006/0253198 A1 * | 11/2006 | Myint et al. | 623/17.12 |
| 2006/0265075 A1 | 11/2006 | Baumgartner et al. | |
| 2007/0038301 A1 * | 2/2007 | Hudgins | 623/17.16 |

OTHER PUBLICATIONS

European Patent Office, Invitation to Pay Additional Fees with Partial Search Report, dated Jun. 15, 2007, 6 pgs.

* cited by examiner

DEVICES AND METHODS FOR DISC REPLACEMENT

CROSS REFERENCE TO RELATED APPLICATIONS

This is a continuation application that claims the benefit under 35 U.S.C. § 120 of non-provisional U.S. patent application Ser. No. 11/332,622, filed Jan. 13, 2006. The aforementioned application is hereby incorporated by reference for all purposes.

FIELD OF THE INVENTION

Embodiments of the present invention relate generally to disc replacement therapy. More particularly, embodiments of the present invention relate to methods, devices and materials that may be used in disc replacement therapy procedures.

BACKGROUND

The spinal column consists of a complex system of bones and connective tissues that provides support for the body and protects the delicate spinal cord and nerves. The spinal column includes a series of vertebrae stacked one on top of the other, each vertebral body includes an inner or central portion of relatively weak cancellous bone and an outer portion of relatively strong cortical bone. Situated between each vertebral body is an intervertebral disc that cushions and dampens compressive forces experienced by to the spinal column. A vertebral canal containing the spinal cord and nerves is located behind the vertebral bodies.

The bones and connective tissue of an adult human spinal column consists of more than 20 discrete bones coupled sequentially to one another by a tri-joint complex which consist of an anterior disc and the two posterior facet joints, the anterior discs of adjacent bones cushioned by intervertebral discs. These more than 20 bones are anatomically categorized as being members of one of four classifications: cervical, thoracic, lumbar, or sacral. The cervical portion of the spine, which includes the top of the spine, up to the base of the skull, includes the first 7 vertebrae. The intermediate 12 bones are the thoracic vertebrae, and connect to the lower spine comprising the 5 lumbar vertebrae. The base of the spine is the sacral bone (including the coccyx). The component bones of the cervical spine are generally smaller than those of the thoracic and lumbar spine. Although complex, the spine is a highly flexible structure, capable of a high degree of curvature and twist in nearly every direction.

Many types of spinal column disorders affect the function and integrity of the spine such as degenerative disc disease, spondylolisthesis (forward displacement of one vertebra over another, usually in a lumbar or cervical spine), scoliosis (abnormal lateral curvature of the spine), kyphosis (abnormal forward curvature of the spine, usually in the thoracic spine), excess lordosis (abnormal backward curvature of the spine, usually in the lumbar spine) and other disorders caused by abnormalities, disease, or trauma, such as ruptured or slipped discs, degenerative disc disease, fractured vertebra, and the like. Patients that suffer from such conditions usually experience extreme and debilitating pain, as well as diminished nerve function.

Spinal pathologies limit the range, and/or threaten the critical elements of the nervous system housed within the spinal column. A variety of systems exist that achieve immobilization by implanting artificial assemblies in or on the spinal column. Lateral and anterior assemblies are coupled to the anterior portion of the spine, which is the sequence of vertebral bodies. Posterior implants generally include pairs of rods that are aligned along the axis which the bones are to be disposed, and which are then attached to the spinal column.

One of the most common motion segment surgical interventions is called arthrodesis, or spine fusion. Clinical success varies considerably, depending upon technique and indications, and consideration must be given to the concomitant risks and complications. For example, it has been shown that spine fusion decreases function by limiting the range of motion for patients in flexion, extension, rotation, and lateral bending. Furthermore, it has been shown that spine fusion creates increased stresses and, therefore, accelerated degeneration of adjacent non-fused motion segments. Also, the fusion device, whether artificial or biological, may migrate out of the fusion site.

While some disc replacement materials and methods currently are known, further improvements are needed. Thus, needs exist for placement of disc replacement materials and structures that may provide support and preserve motion.

SUMMARY

In one embodiment, the present invention relates to a prosthetic structure for replacement of at least a portion of the intervertebral disc nucleus. In some embodiments, use of this structure allows the annulus fibrosis to remain substantially intact. The device includes a bag structure made from a flexible material having a cavity therein. The bag structure includes an opening that is in communication with the cavity, and may include a fixation component, which is adapted to allow fixation to vertebral endplates when placed into the cavity. The bag structure with a fixation component is adapted to remain within an intervertebral disc space without extrusion from the space in one example when the fixation component interacts with vertebral bodies. Further, the bag structure may include an interfacing layer wherein the interfacing layer may be situated between a bag structure and a fixation component. In some embodiments, an interfacing layer reduces the contact between a bag structure and a fixation component.

In some embodiments, a fixation component may include a mechanical structure, a flexible material and/or an agent. In some embodiments, the flexible material may include a semipermeable flexible material. In some embodiments, the flexible material of the bag structure may include a material having a metallic property.

In some embodiments, a bag structure may have a component such as an anchoring component like a flange. Optionally, the flange may contain holes capable of being used to anchor the bag structure to a vertebral body.

Further, in another particular embodiment, the present invention may include implanting a prosthetic bag structure having a fixation component. The annulus may be partially resected, a substantial portion of the disc nucleus may be removed to create a cavity. Vertebral endplates may be prepared by any known method in the art. In accordance with this particular embodiment, a bag structure having a fixation component may be introduced to the cavity and configured to receive an interior implant structure.

In yet another embodiment, the present invention relates to another method for implanting a prosthetic structure into an intervertebral space. In accordance with this embodiment, the annulus may remain substantially intact by cutting the annulus to form an opening that is capable of being repositioned to substantially its original position.

A more complete understanding of the present invention may be derived by referring to the detailed description of preferred embodiments and claims when considered in connection with the figures.

BRIEF DESCRIPTION OF THE DRAWINGS

In the Figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

DETAILED DESCRIPTION

Embodiments of the present invention relate generally to devices, materials and methods for replacing at least a portion of an intervertebral disc nucleus and in other embodiments replacing all of an intervertebral disc nucleus. More particularly, embodiments of the present invention relate to disc nucleus prosthesis structures, including prosthesis bag structures, implant structures, and a combination of prosthesis bag structures and implant structures. While various prosthetic structures discussed herein are presented with reference to replacement of part or all of a human disc, embodiments of the present invention have application beyond human disc replacement. For example, the prosthetic structures discussed herein could be used in or with discs for any suitable vertebrate animal that might need of a disc replacement.

Figure 1:
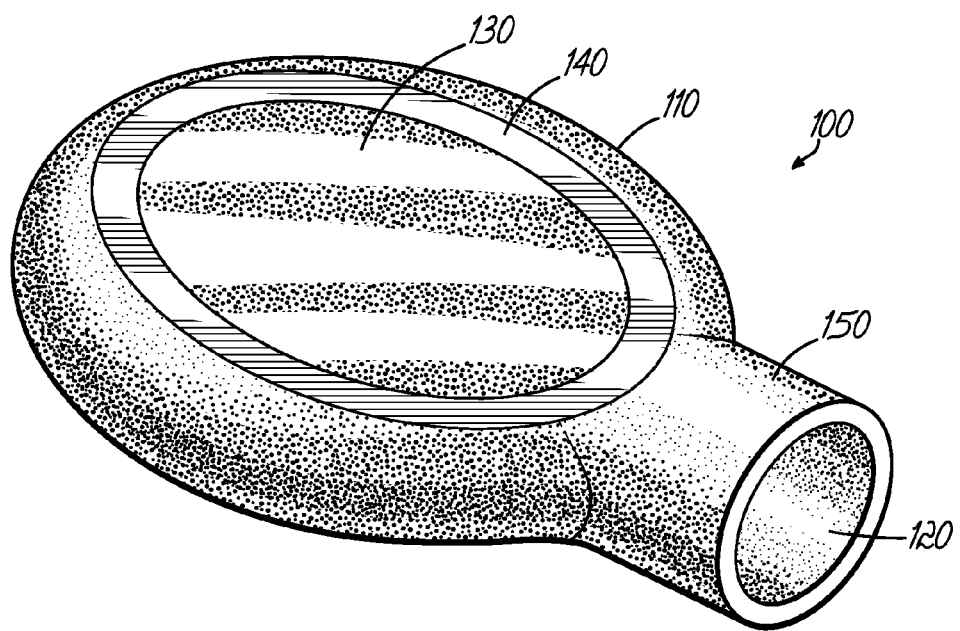
FIG. 1 represents a schematic diagram of an implant bag structure.
Figure 3:
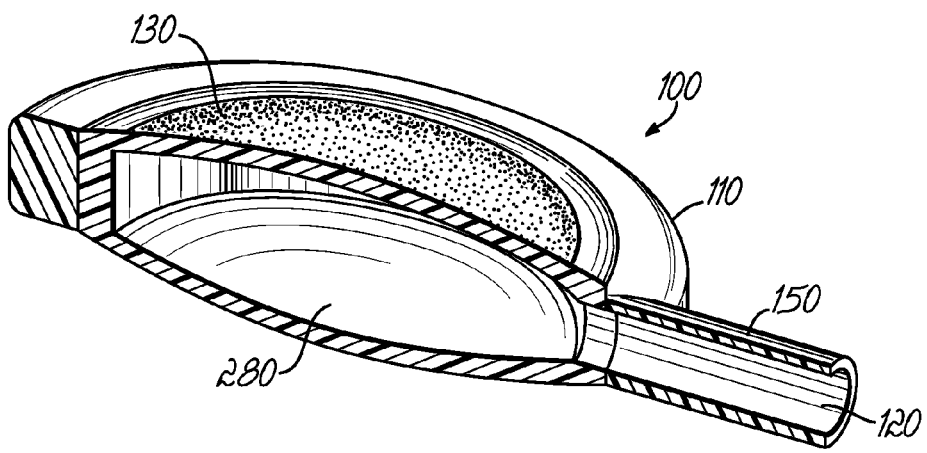
FIG. 3 is an isometric view partially in cross-sectional view of one embodiment of an intervertebral disc nucleus prosthetic bag structure in accordance with the present invention.
Figure 4:
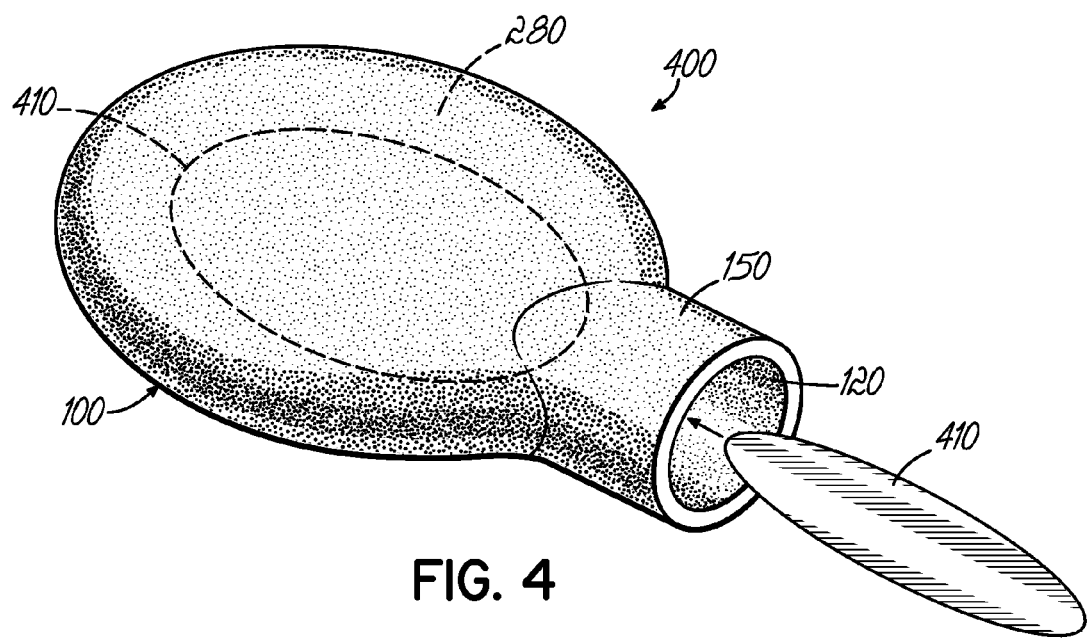
FIG. 4 is an isometric view of one embodiment of an intervertebral disc nucleus prosthetic bag structure having an implant structure positioned therein in accordance with the present invention.

Referring now to FIGS. 1 and 3, one embodiment of the present invention includes an intervertebral disc nucleus prosthetic bag structure 100 that may be used for replacing all or part of a diseased, damaged or otherwise non-functional intervertebral disc nucleus. In one embodiment, bag structure 100 includes an outer body 110, an optional porous fixation plate or component 130, an optional interfacing layer 140, an access port 150 and opening 120 for receiving, for example, an interior implant structure or material.

In accordance with one embodiment of the invention, bag structure 100, and in particular, outer body 110 is formed of a flexible material. In other embodiments, a fixation component 130 may be part of or separate from bag structure 100. For example, fixation component 130 may be associated with upper and lower surfaces of bag structure 100. Fixation component 130 may be introduced to bag structure 100 subsequent to an interfacing layer 140 which may be made of a material such as a polymer. Interfacing layer 140 may serve as an adhesive between the fixation component 130 and the outer surface of an implant structure such as bag structure 100. In addition, interfacing layer 140 may be used to reduce contact between the outer surface of bag structure 100 and fixation component 130. This separation reduces surface contact between fixation component 130 and bag structure 100 that may lead to destruction of an implant structure due to for example contact agitation.

While fixation component 130 has several functions, one function of fixation component 130 may be to decrease the movement of the prosthetic implant within a disc nucleus by inducing intervertebral fixation such as inducing bone ingrowth. Reduction in the movement of the implant structure once placed within a nuclear space may preserve relative motion of a subject receiving such an implant by reducing relative motion of the implant and vertebral endplates. In addition, fixation component 130 once fixed to vertebral endplates is capable to transmitting transverse in-plane shear loads. To induce fixation of any prosthetic implant to intervertebral bodies disclosed herein any known methods for preparing vertebral endplates may be used.

In some embodiments, bag structure 100, and in particular, outer body 110 and fixation component 130 may be formed of a semi-permeable flexible, resilient, elastic or viscoelastic material. Some of these materials may have a time dependent deformation quality that dissipates some mechanical energy; thus, there is a viscoelastic quality to the material in some of these examples. Therefore, bag structure 100 and fixation component 130 may be compressed, to facilitate implantation in an annulus fibrosis cavity using a delivery device, such as a catheter or the like. Once inserted into the intervertebral space, bag structure 100 and the fixation component 130 may be released from the delivery device, so that it returns to its relaxed unstretched state. Implantation of the bag structure will be discussed in more detail below.

In one embodiment, fixation component 130 of bag structure 100 may be formed of an immunologically inert material that is compatible with the environment found within a mammalian body, and in particular, within an intervertebral disc. As one skilled in the art will appreciate, the immunologically inert material does not induce any significant response by the immune system when the structure is implanted into a subject. Fixation component 130 may be formed of one or more materials, including in some embodiments, one or more porous materials. In addition, outer body 110 of bag structure 100 may be formed from one or more layers of material such as a layer to reduce leakage and/or a layer for fixation. In addition, the shape of the bag structure 100 as viewed from the top may be circular, oval, or other shapes that may fit the shape of the intervertebral space. In addition, the implant may include an eccentricity ratio of about 1.0 to 2.0 in the transverse plane of the disc space, or, in alternative embodiments, may include an eccentricity ratio of about 1.0 to about 3.5.

In one embodiment, fixation component 130 may be formed of one or more different materials, which exhibit porous properties. That is porous material of fixation component 130 that induce ingrowth of cellular material such as bone ingrowth as discussed previously. In addition, fixation component 130 may be coated with an agent. For example, an agent for coating fixation component 130 may include a biological agent capable of increasing the likelihood of inducing ingrowth of physiological components. For example, calcitonin or other biological or non-biological agents may be used as agents to coat fixation component 130.

Structural Bag

In some embodiments, any structure such as a bag structure or fixation member of the present invention including bag structure 100 may be formed of one or more different materials, which exhibit semi-permeable, flexible, resilient and/or elastic properties. These materials are discussed in the following paragraphs. In one example, the material of bag structure 100 is such that it is capable of being easily stretched, expanded or compressed, and then resuming its former shape or close to its former shape (U.S. patent application Ser. No. 11/201,837, incorporated herein by reference in its entirety). In one embodiment, a bag structure 100 may be formed from a woven or non-woven polymeric fiber material, such as, an aramid material (e.g., Kevlar™, Nomex™, Twaron™, etc.), a polyester fiber material, an ultra high molecular weight polyethylene fiber material, a nylon fiber material, a cellulose fiber material, a polyurethane fiber material, or a polyacrylonitrile based fiber material. In another embodiment a bag structure made of woven material may have a dome shape to the top and/or bottom part of the bag. In accordance with this embodiment, a dome of the bag can be thick and resilient in order to ease transition of the adjacent natural environment and an implant device. In some embodiments the polymeric fiber material may be woven or configured into a 2-dimensional or 3-dimensional fabric configuration. In accordance with these embodiments the weave may be a honeycomb weave. The weave pore size may vary as a function of fabric density.

In another embodiment of the present invention, bag structure 100 may be made and/or formed from a metallic material, such as nitinol, stainless steel (e.g., heat—treated PH 17-7 stainless steel fabric) or the like. In still other embodiments, bag structure 100 may be made and/or formed from metallic fibers woven into a fabric-type material. In some embodiments, the fabric-type material may be a 2-dimensional or 3-dimensional fabric configuration.

In further embodiments, bag structure 100 may be made of a combination of materials. For example, one combination might be a combination of a polymeric fiber and a metallic material; e.g., an aramid material (e.g., Kevlar or the like) and a metallic material (e.g., nitinol, stainless steel).

In another embodiment of the present invention, bag structure 100 may be made of a semi-permeable, flexible, composite material, such as a composite of an elastomeric or hydrogel matrix material and a polymeric fiber, a metal fiber or wire, or a ceramic fiber. Examples of suitable matrix materials that may be used to form bag structure 100 include, but are not limited to, a natural or synthetic polymer matrix material, an elastomer, a flexible polyolefin polymer, an elastomeric matrix material, or a hydrogel material.

Discussed above are various examples of classes of materials that may be used to form bag structure 100 as well as other structures of the present invention. Other specific materials that may be used to make bag structure 100 include, but are not limited to, polyaramid fibers, such as Kevlar 49, Kevlar 149- or the like, ultra high molecular weight, highly oriented, highly crystalline polyethylene (e.g., Dyneema or Spectra 900 or Spectra 1000), polyester fibers, such as Dacron, silk fiber, elastin fiber, elastomeric materials (polyurethane or other thermoplastic elastomer), fused PTFE (Polytetrafluoroethylene), expanded PTFE of generally high tenacity fibers or other high strength woven or non-woven fibers or fabrics. It is also contemplated that any embodiment of the present invention may be accompanied by vertebrolasty to increase the strength of any weakened vertebrae including but not limited to disease, aging or injury.

Figure 2A:
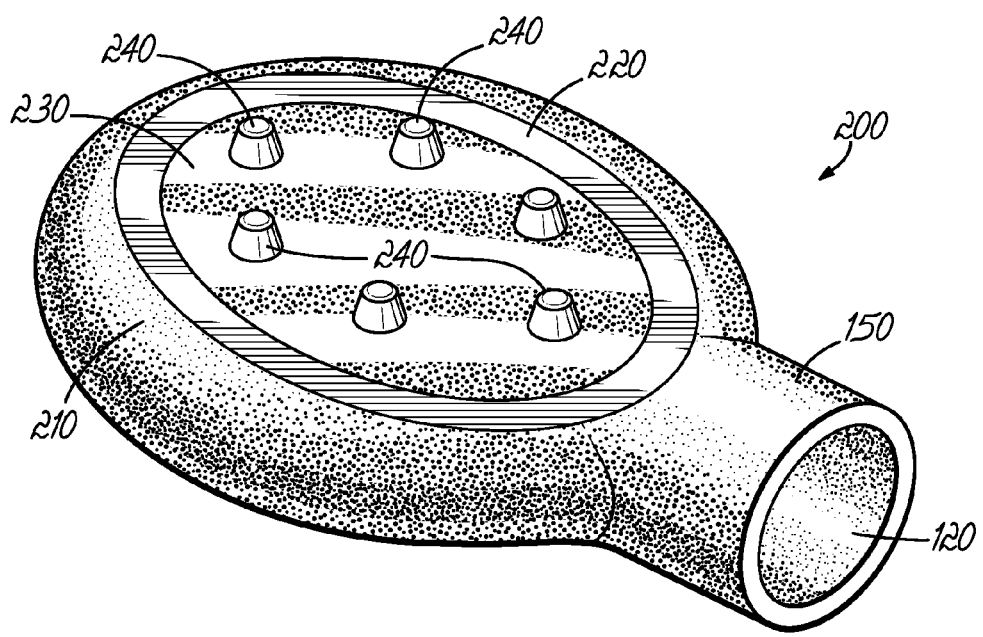
FIG. 2A represents a schematic diagram of an implant structure in accordance with one embodiment of the present invention.
Figure 2B:
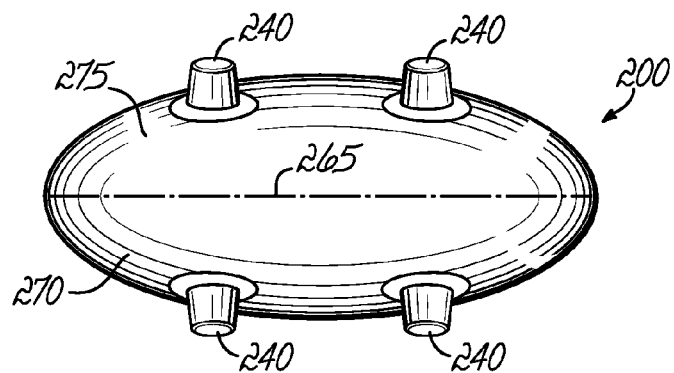
FIG. 2B is a three dimensional side view of an implant structure in accordance with one embodiment of the present invention.
Figure 2C:
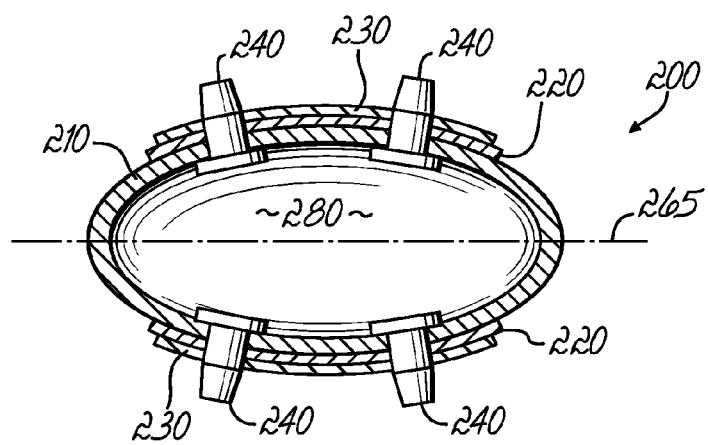
FIG. 2C is a cross-sectional view of the intervertebral disc nucleus prosthetic bag structure in accordance with one embodiment of the present invention.

Referring now to FIGS. 2A, 2B and 2C, one embodiment of the present invention includes an intervertebral disc prosthetic bag structure 200 that may be used for replacing all or part of a diseased, damaged or otherwise non-functional intervertebral disc. In the illustrated embodiment, bag structure 200 includes an outer body 210 and a fixation member 240 including at least one fixation member that extends exteriorly from the outer body 210. Fixation member 240 may be optionally attached to a fixation layer 230, and an optional interfacing layer 220 may separate fixation layer 230 from outer body 210, an access port 150 and opening 120 for receiving, for example, an interior implant structure or material. Alternatively, fixation layer 230 and interfacing layer 220 may include one layer instead of two separate layers.

In accordance with some embodiments of the invention, any of the structures such as bag structure 200, and in particular, fixation member 240 is formed of a rigid material or a flexible material as detailed previously. In other embodiments, fixation layer 230 and fixation member 240 may be attached to upper and lower surfaces 275,270 of a bag structure (265 depicts an optional bag axis). Fixation member 240 may be attached using an interfacing layer 220 such as a polymer interfacing layer as discussed. Fixation member 240 may be attached to fixation layer 230 where fixation layer 230 may be in contact with interfacing layer 220. Alternatively, fixation member 240 may be optionally coated with an agent such as an agent to induce bone ingrowth. Examples of agents for inducing bone ingrowth might include but are not limited to cellular components such as growth factors, other proteins, matrix material, gel material or other known agents.

In addition, fixation member 240 may be a retainer made of a biocompatible material and may include but is not limited to a rivet, a brad, a screw, spike, dowel, pin or a combination thereof. In another example, fixation member 240 may be used to hold layers together such as fixation layer 230, interfacing layer 220 and outer body 210 depicted in FIG. 2C. In some embodiments, fixation member 240 may be used to place bag structure 200 in close association with vertebral bodies and reduce gaps between bag structure 200 and vertebral bodies. For example, fixation member 240 may be a rivet introduced to bag structure 200 from the inner cavity 280 of a bag structure 200 and extend exteriorly outward from the bag where one end of fixation member 240 is adapted for positioning in vertebral bodies. Fixation member 240 is capable of several functions, such as reducing separation of layers such as outer body 210, interfacing layer 220 and fixation layer 230 as well as providing direct contact between fixation member 240 and intervertebral bone in order to increase communication between the prosthetic implant structure and vertebral bodies.

In some embodiments, it is contemplated that any component in the present disclosure may be made of a flexible material as discussed previously. With this in mind, the later prosthetic implant structure having fixation member 240 may have a time dependent deformation; thus, there is viscoelastic quality to the material in some of these examples. Therefore, bag structure 200 having fixation member 240 may be compressed, so that it may be implanted in an intervertebral disc space cavity using a delivery device, such as a catheter, stylet or the like. Once inserted into the intervertebral space, bag structure 200 having fixation member 240 may be released from the delivery device, so that it returns to its relaxed state. Alternatively, bag structure 200 having fixation member 240 may be placed into an intervertebral space using, for example, a pair of forceps or other known method for placement.

In one embodiment, fixation member 240 may be positioned on top 275 and on bottom 270 of the bag structure to increase the likelihood of contact of fixation member 240 with vertebral bodies (see FIG. 2B. In another embodiment, fixation member 240 may be positioned on top 275 and on bottom 270 of bag structure 200 wherein fixation member 240 on the top 275 is substantially symmetrical to fixation member 240 on bottom of the bag structure as shown in FIG. 2B. Implantation of the bag structure will be discussed in more detail below.

One advantage of fixation member 240 or fixation layer 230 is gross relative motion may be reduced between an implant device and vertebral endplates and reduction of this motion may increase support in transverse shear loads. In addition, device 200 is capable of being reduced in size and implanting the device may occur with less surgical trauma.

Surveying and Sizing

It is contemplated that any one of the prosthetic implant structures disclosed herein may be introduced in a similar fashion as described for bag structure 100 or may be introduced using other known methods in the art. In addition, it is contemplated herein that any known method for assessing a cavity or estimating a size needed for an implantation structure may be used for any embodiment of the present invention. In some embodiments, once the nucleus is removed in preparation for implantation of a prosthetic device, a deployment device may be used to assess the cavity condition prior to introduction of any implant structure. For example, a balloon catheter may be introduced to the cavity and filled with an agent such as a contrast solution and the area viewed with an instrument such as an X-ray, c-arm, intraoperative CT-scan or the like. A healthcare professional may view the cavity to assess whether the area is ready for the insertion of the prosthetic implant or requires additional preparation. It is contemplated that any sizing device known in the art may be used to assess the size and dimensions of an implant device needed for disc replacement.

In accordance with one embodiment of the present invention, once the nucleus material is removed, a delivery device (e.g., a cannula or other catheter device) may be used to introduce bag structure 100 having a fixation component 130 (see FIGS. 1 or 3) into the annulus cavity. In one embodiment, bag structure 100 may be stretched and/or compressed and then attached to the delivery device so that it may be delivered through an opening in the disc annulus into the disc nucleus region. For example, in one embodiment, bag structure 100 is compressed into a cannula or onto a catheter, and then delivered into the nucleus region using a balloon catheter delivery technique, or the like. After the bag structure 100 having a fixation component 130 is delivered into the nucleus region, it is released. In some embodiments, upon release, bag structure 100 will expand to substantially its uncompressed original shape.

In other embodiments, a balloon device (e.g., balloon catheter device) may be used to deploy bag structure 100 within the disc nucleus region. As one skilled in the art will appreciate, during a balloon catheter delivery procedure, a balloon catheter is used to place bag structure 100 within the disc nucleus, and then a balloon is inflated within the bag structure 100, causing the compressed bag structure to expand to its original or close to original shape. In one embodiment, bag structure 100 having a fixation component 130 may be deployed using a balloon catheter such that deploying the bag may position the fixation component of the bag near or in close proximity to the vertebral bodies. In another embodiment, deploying bag structure 100 having a fixation component 130 can position the fixation component in direct contact with the vertebral bodies. In one example, the fixation component 130 is coated by an agent such as a biological agent for example, calcitonin or the like. Once bag structure 100 is expanded, the balloon is deflated and then removed.

In some embodiments, an interior implant material and/or structure may be placed into a cavity 280 of any bag structure (see FIGS. 1-4) such as bag structure 100 through the opening 120 so that the combination of bag structure 100 and interior implant material 410 provide a resilient disc nucleus prosthesis 400. In some embodiments, interior implant material or structure 410 conforms to at least a portion of the interior cavity 280 of bag structure 100, thus providing additional spinal support within the intervertebral space. In accordance with some embodiments of the invention, interior implant material or device 410 may be, for example, a hydrogel implant, a spiral implant, a biological implant, a hydratable material. the implant structure discussed below, or any other suitable disc implant material or device. In one embodiment, the interior implant material and/or device may be, for example, a sinusoidal-shaped structural device disclosed in U.S. patent application Ser. No. 11/201,837, which is incorporated herein by reference in its entirety. Further, in other embodiments, the sinusoidal-shaped structural device discussed below may be implanted or positioned within bag structure 100. Alternatively, bag structure 100 outer body may be coated with an agent such as a polymer (e.g. polyurethane) to reduce leakage of an interior implant introduced to bag structure 100. The implantation of this device in a bag structure will be discussed in more detail below.

In yet another embodiment of the present invention, an interior implant structure may include a structure capable of being fed into an opening in the bag structure such that the bag cavity may be fed the interior implant until the bag cavity is substantially filled. Then, the remaining interior implant structure is severed from the implanted portion. Then, the bag opening may be sealed to reduce escape of the interior implant.

Different delivery devices and/or methods may be used to insert the interior implant into the bag structure, and the delivery devices and/or methods used may differ depending on the type of implant material or structure used. After the interior implant material and/or structure is placed within bag structure 100, opening 120 of bag structure 100 then may be sealed or closed, thus reducing extrusion of interior implant material and/or structure from within a bag structure. As one skilled in the art will appreciate, any sealing or closing process and/or device may be used to seal the bag structure, such as suturing, clamping, tying, using a single directional opening valve or the like.

Figure 5:
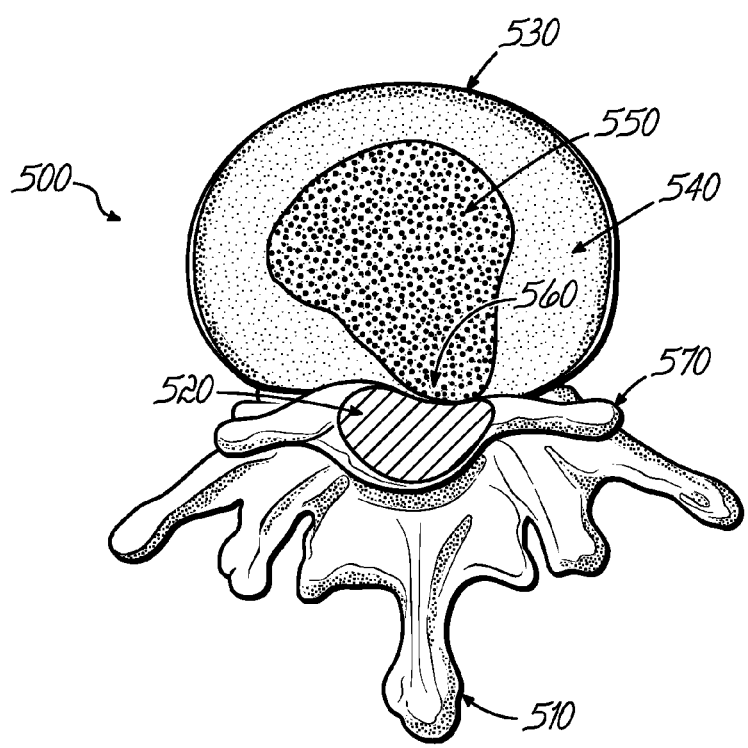
FIG. 5 is a cross-sectional view of a spinal column showing a herniated disc.

Referring now to FIG. 5, a cross-sectional view of a spinal column 500 having a herniated disc or damaged disc is shown. In the illustrated embodiment, the cross-section shows a vertebrae 510, a spinal cord 520 with nerve roots 570, and a disc 530, having an annulus 540 and a disc nucleus 550. As is illustrated by location 560 in FIG. 5, a herniated disc occurs when disc nucleus 550 protrudes an opening or weakness in annulus 540. The annulus or extruded nucleus may put pressure on spinal cord 520 and/or nerve roots 570. When this occurs, one remedy is to remove the protruding disc annulus and/or nucleus and replace it with a prosthetic nucleus or total disc structure and/or material. These procedures are known in the art, and thus, will not be discussed in detail herein.

Figure 6A:
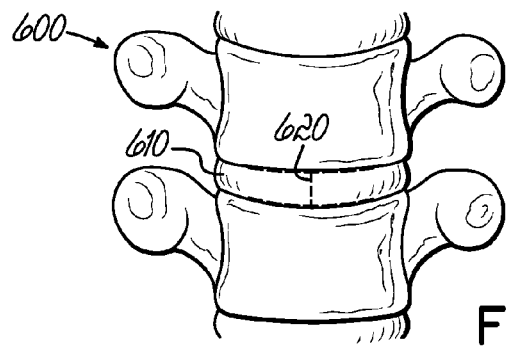
FIGS. 6A-6D are schematic representation of implantation of a prosthetic device in accordance with one embodiment of the present invention.
Figure 6B:
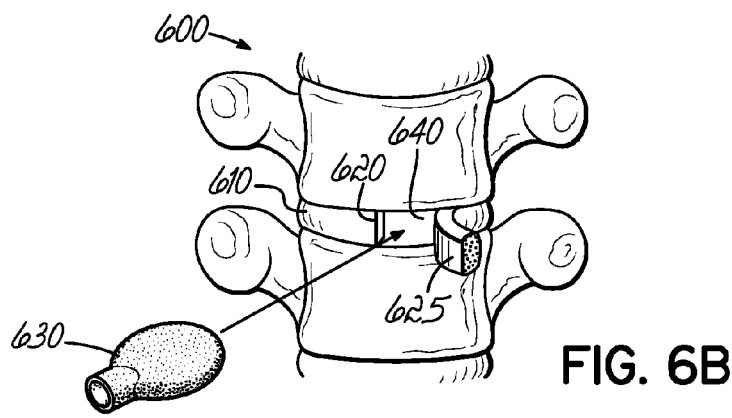
Figure 6C:
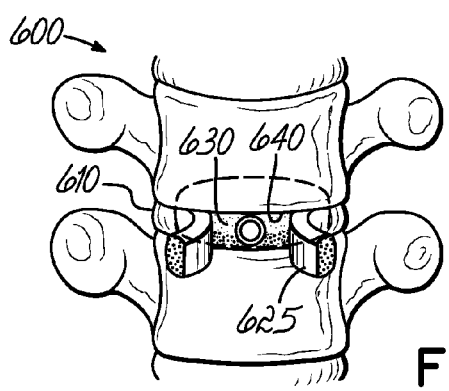
Figure 6D:
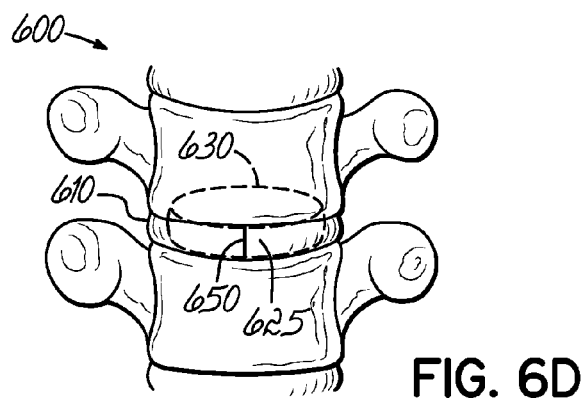

Referring now to FIGS. 6A-6D, one embodiment of the present invention includes implantation for an intervertebral disc prosthesis structure where at least a portion of the disc nucleus is removed and the annulus may be cut forming an opening. This method of implantation may preserve the integrity of the annulus and may also reduce scarring typically complicating other implantation methods. Reduction in scarring may reduce the likelihood of impaired movement and pain. In addition, preserving the annulus structure may also reduce adhesion and scarring due to typical post-implantation healing and recovery, especially with respect to total disc replacement. In accordance with this embodiment of the invention and as depicted in FIGS. 6A and 6B, cuts 620 are made in the annulus 610 to produce a movable portion 625 in the annulus 610 such as a flap, hatch, door, double-door and the like with minimal or no removal of annulus tissue. In accordance with this embodiment, the movable annulus portion 625 may be adapted for use in any procedure that requires access to a disc region. In one embodiment, an opening 640 accessed by opening movable annulus portion 625 may be of a predetermined size and/or a size based on dimensions for implantation device 630. The prosthetic structure and/or material 630 may be placed within the annulus 610 where the nucleus material was removed, as shown in FIG. 6C, and annulus 610 may be sealed 650, as shown in FIG. 6D, by any means known in the art such as suturing, stapling, tacking with a biocompatible adhesive agent or the like.

Figure 7:
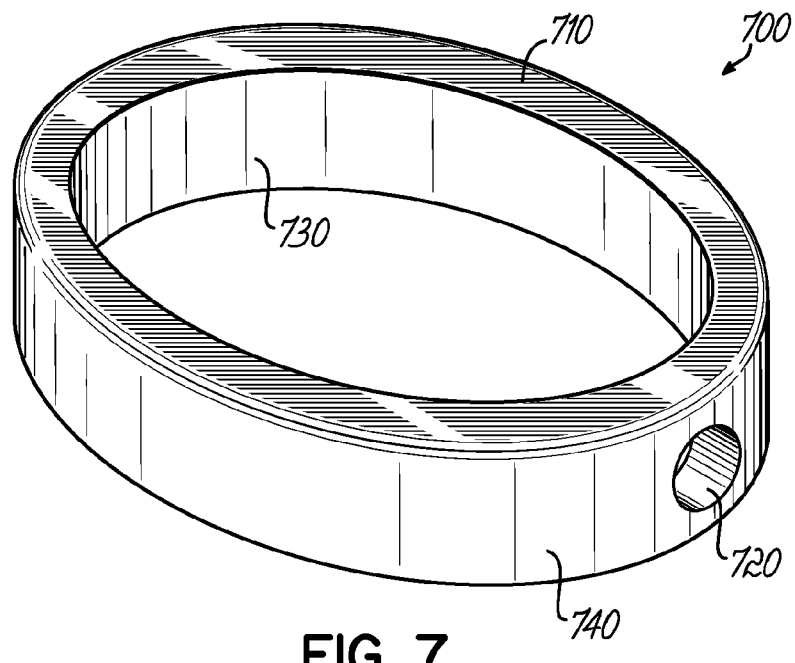
FIG. 7 is a perspective view of a component of an implant structure in accordance with one embodiment of the present invention.
Figure 8A:
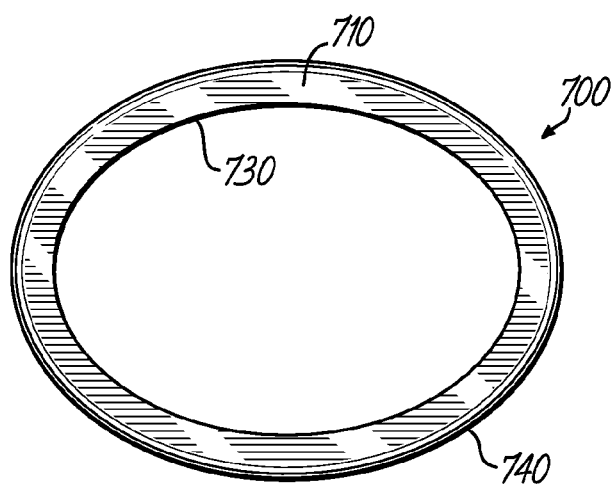
FIG. 8A is a top view of the component depicted in FIG. 8A in accordance with one embodiment of the present invention.
Figure 8B:
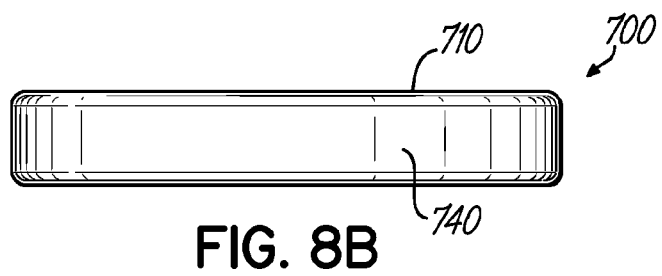
FIG. 8B is a side view of the component depicted in FIG. 8A in accordance with one embodiment of the present invention.

Referring now to FIGS. 7, 8A and 8B, one embodiment of the present invention includes removal of a substantial portion of a disc annulus prior to implantation of an intervertebral disc prosthetic structure 700. Implant structure 700 includes an upper and lower substantially flat surface 710, an interior surface 730, an exterior surface 740 and an access port 720. Implant structure 700 may be a thick-walled textile structure of a single layer of material or a combination of several layers of material. In accordance with one embodiment of the invention, implant structure 700 may be made of a series of flat donut-shaped rings laying one on top of the other for example using fabrics such as Offray Specialty fabrics, honeycomb weave fabrics or other 2 or 3 dimensional fabrics. It is contemplated herein that any fabric used to make implant structure 700 may be made of any resilient material that permits springing, cushioning, bending, and rotation.

Figure 9:
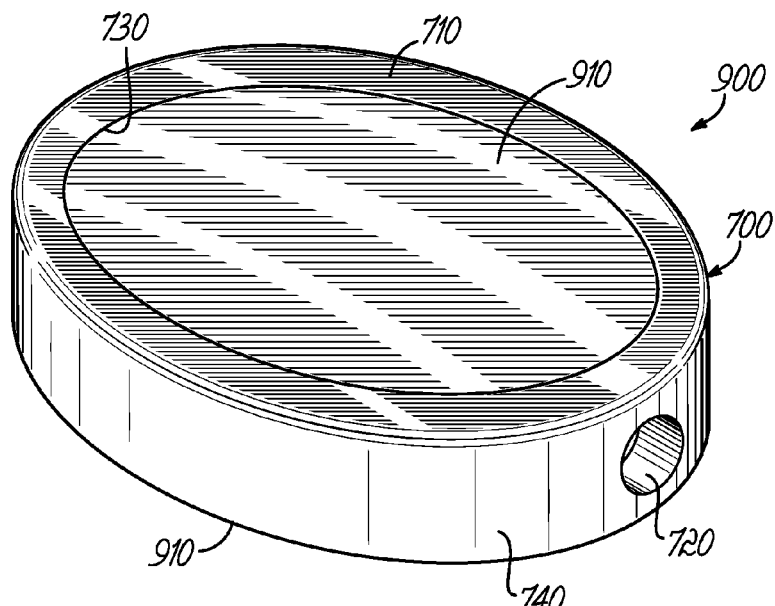
FIG. 9 is a perspective view of an implant structure in accordance with one embodiment of the present invention.

In one embodiment, implant structure 700 may be combined with a membrane-like component 910 to provide an intervertebral implant 900 depicted in FIG. 9, where implant structure 700 provides a flat surface 710 for engaging endplates such as vertebral endplates where the endplates are in close proximity to the flat surface 710 of implant 900. In addition, implant structure 700 may be used to anchor the membrane-like component 910 such as any membrane material identified for use on bag structure 100. Optionally, once an implant 900 with flat surface 710 and membrane component 910 is introduced to the intervertebral space, inner cavity 730 may be filled via access port 720 with, for example, a polymer such as an elastomer, hydrogel, in situ curable hydrogel or the like. It is contemplated herein that in some embodiments membrane 910 is expandable to substantially conform to the disc space. This expansion may occur on the upper and lower surfaces of membrane 910 of intervertebral implant 900. In another embodiment, flat surface 710 may be bonded with a metal fiber such as trabecular metal to increase fixation of intervertebral implant 900 with intervertebral bodies.

Figure 10A:
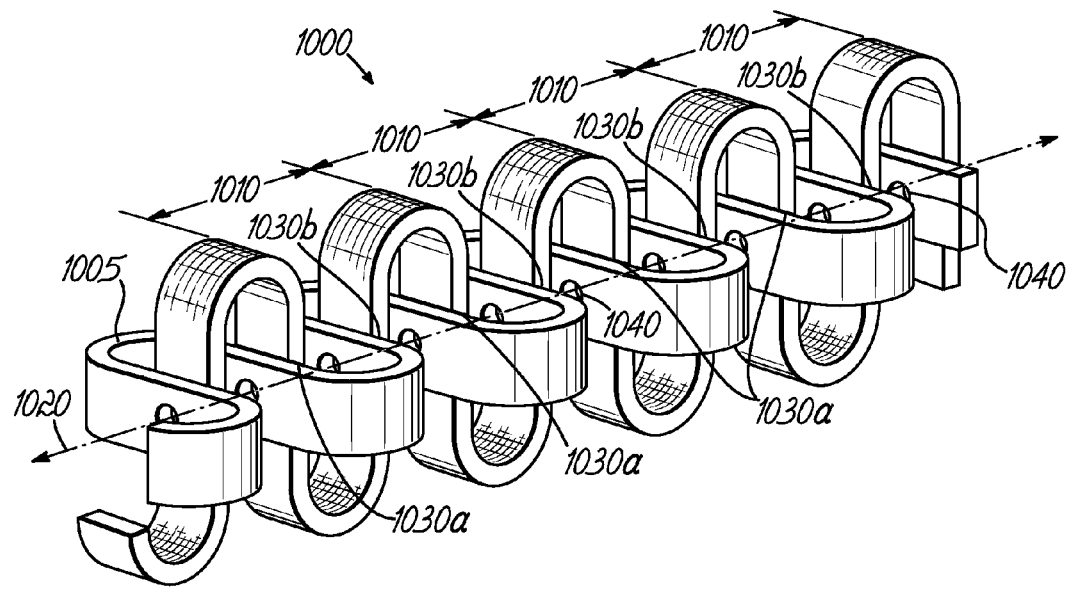
FIGS. 10A and 10B are perspective views of an interior implant structure in accordance with some embodiments of the present invention.
Figure 10B:
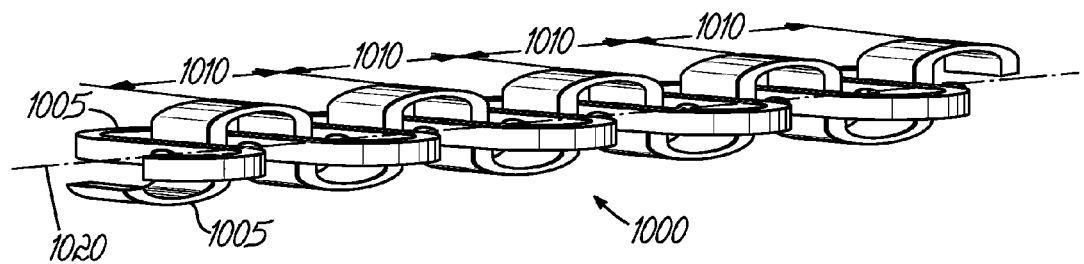

Referring now to FIGS. 10A and 10B, one aspect of the present invention relates to an interior implant structure, which may act as a portion of a disc replacement prosthesis, or at least as an interior portion of a disc prosthesis structure; one embodiment of which is illustrated in FIGS. 10A-10B (U.S. patent application Ser. No. 11/201,837, incorporated herein by reference in its entirety). In the illustrated embodiment, interior implant structure 1000 includes one or more sinusoidal-shaped structures 1005. In accordance with this particular embodiment of the invention, each sinusoidal-shaped structure 1005 includes a plurality of periodic portions 1010, which are formed of a flexible, resilient, elastic material similar to the material discussed previously for bag structure 100. As illustrated in FIGS. 10A-10B, each periodic portion 1010 intersecting a longitudinal axis 1020 of the interior implant structure 1000 at two points, 1030a and 1030b. In one embodiment, the sinusoidal-shaped structures 1005 are flexible, such that when stretched in a longitudinal direction (i.e., along axis 1020), the structure sufficiently flattens or otherwise reduces the amplitude of each of the periodic portions 1010, so that it may be placed within a disc nucleus region or holding structure within the disc nucleus region (e.g., bag structure 100, discussed above). FIG. 10B illustrates one embodiment of interior implant structure 1000 (i.e., sinusoidal-shaped structures) in a stretched configuration.

As illustrated in FIG. 10A and FIG. 10B, one embodiment of the invention may have multiple sinusoidal-shaped structures 1005 positioned together, or otherwise interwoven with each other. The embodiment illustrated in FIG. 10A and 10B show two sinusoidal-shaped structures 1005 interwoven or otherwise joined and positioned in planes that are positioned at or near 90 degrees from one another. In other embodiments, two sinusoidal-shaped structures 1005 may be positioned in different planes that are not necessarily perpendicular to one another. In still other embodiments, more than two sinusoidal-shaped structures 1005 may be used. In another example, a sinusoidal-shaped structure may be introduced to bag structure 100 where the sinusoidal-shaped structure is loaded into the cavity until bag structure 100 is substantially filled with the interior implant and then the excess sinusoidal-shaped structure is removed. Removal of excess sinusoidal-shaped structure may include any known method in the art such as cutting off the unused portion of structure 1000. In accordance with embodiments of the invention, sinusoidal-shaped structures 1000 may be reduced in volume and loaded onto a delivery device such as a cannula or forceps for delivery to the intervertebral space or cavity.

In one embodiment, interior implant structure 1000 may be inserted into a bag structure (e.g., bag structure 100) located in the intervertebral cavity using an external delivery device, such as a cannula, a catheter, or other suitable delivery device. In accordance with one embodiment, a delivery device may be inserted through holes 1040 in sinusoidal-shaped structures 1005, and then the structures may be stretched along the delivery device to reduce the height or amplitude of the sinusoidal-shaped devices, as discussed above. Once the height of the structure is sufficiently reduced, it may be positioned or placed within the internal cavity 280 of bag structure 100, for example, through opening 120 in bag structure 100. Once inside a bag structure, interior implant structure 1000 (i.e., sinusoidal structures 1005) is released from the delivery device, which will allow structures 1000 to relax and return back to or near its original shape, thus filling the bag structure and at least a portion of the disc cavity regions.

In some embodiments, a coating agent may be applied to a structure (e.g., bag structure 100) and/or an interior implant structure (e.g., interior implant structure 1000). In one embodiment, the coating agent may include one or more of hydrogel, a curable biomaterial that changes states once introduced to the intervertebral disc region (e.g., by chemical or heat promotion), elastomers (e.g., thermoset and thermoplastic), polyolefins, therapeutic agents (e.g., anti-bacterial or anti-fungal agents or biological agents). Biological agents may include, for example, tissue extracts, cells (e.g., bone derived cells), growth factors (e.g., platelet derived growth factor (PDGF)), proteins (e.g., the hormone calcitonin) or genes (e.g., nerve growth or bone growth promoting genes).

Figure 11:
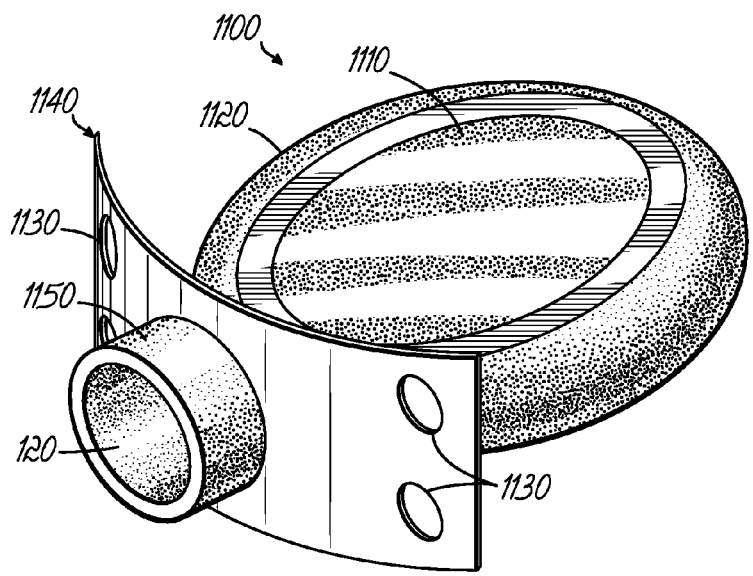
FIG. 11 is a fragmentary view of an implant structure in accordance with one embodiment of the present invention.

Referring now to FIG. 11, one embodiment of the present invention includes removal of a portion of a disc annulus prior to implantation of an intervertebral disc nucleus prosthetic structure 1100 that may be used for replacing part of a diseased, damaged or otherwise non-functional intervertebral disc nucleus. Implant structure 1100 includes a flange structure 1140, optional holes 1130 in the flange, a bag structure 1120 with an optional fixation component 1110, and an access port 1150. In accordance with one embodiment, implant structure 1100 may be combined with any known interior implant structure for example a sinusoidal-shaped implant structure, a hydrogel, and/or a hydratable material (e.g., a hydratable hydrogel material).

Figure 12:
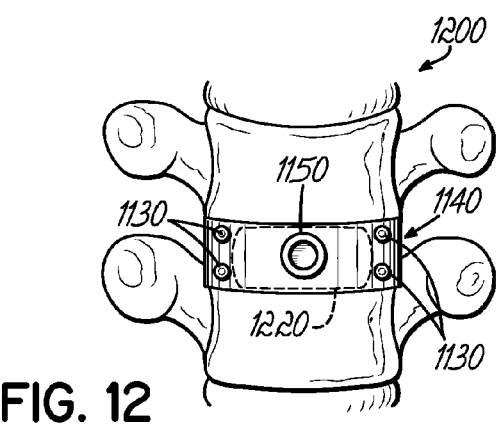
FIG. 12 is a view of an implant structure positioned between two adjacent vertebral bodies in accordance with one embodiment of the present invention.

Referring now to FIG. 12, one embodiment of the present invention includes implantation for an intervertebral disc prosthesis structure. In accordance with this embodiment of the invention, implantation device 1100 having flange 1140 may be introduced to cavity 1220 and optionally anchored to vertebral bodies using, for example, rivets through flange holes 1130. In another embodiment, flange holes 1130 may be used to increase attachment of physiological components to implantation device 1100 such as bone regeneration components. In accordance with this embodiment, bone may grow into and around flange hole 1130 thus inducing attachment of implantation device 1100 to the vertebral disc. To further induce the ingrowth of bone, flange hole openings may be coated with a biological agent to recruit physiological components to flange 1140. Alternatively, flange 1140 may adhere to vertebral bodies using any known adhesive such as a biocompatible adhesive. In another embodiment, implantation device 1100 may be made of any bag structure material previously discussed such as a elastic or viscoelastic material. In accordance with this embodiment, implantation device 1100 may be reduced in size for introduction to a cavity for example by stretching or folding flange 1140 onto the remaining components of implantation device 1100 and loading it onto a delivery device for introduction to a cavity and then resume its original shape or near original shape once released from the delivery device. In addition if required, flange 1140 may be unfolded and aligned exterior to the nucleus region using a device such as forceps. Once implantation device 1100 is within a cavity, any known interior implant material may be added. Optionally, an interior implant material such as sinusoidal material 1000 may be introduced within an interior cavity of implant device. Implant device 1100 may be sealed by any means known in the art such as suturing, tacking with a biocompatible adhesive agent or the like.

The foregoing discussion of the invention has been presented for purposes of illustration and description. It is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights, which include alternative embodiments, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of implanting a prosthetic structure into an intervertebral space comprising:
   selecting a disc having a nucleus;
   removing a substantial portion of the nucleus of the disc to create a cavity; introducing
   to the cavity a bag structure comprising an opening for receiving an interior implant structure, a fixation component comprising a flexible material, and a flange capable of anchoring the bag structure to a vertebral body;
   deploying the bag structure in the cavity;
   anchoring the bag structure to a vertebral body using the flange;
   introducing an interior implant structure to the bag through the opening; and
   sealing the opening of the bag structure;
   wherein introducing the interior implant structure includes a non-helical sinusoidal-shaped structure having periodic portions formed of a flexible material, and wherein introducing the interior implant structure in the bag structure comprises:
   stretching the interior implant structure in a longitudinal direction to reduce the amplitude of the periodic portions of the structure to be able to fit the interior implant structure into the opening of the bag structure;
   loading the interior implant structure onto a delivery device;
   inserting the interior implant structure into the bag structure using the delivery device;
   loading the interior implant structure within the bag structure until the bag structure is substantially filled;
   releasing the interior implant structure from the delivery device within the bag\structure wherein the flexible nature of the material causes the stretched interior implant structure to substantially resume its unstretched state within the bag structure; and
   removing excess interior implant structure.

2. The method of claim 1, further comprising anchoring the implant structure to the flange.

3. The method of claim 1, wherein introducing the bag structure having a flange to the cavity comprises introducing the bag structure in a first reduced conformation and then allowing the flange and bag structure to assume a second conformation with the flange extending exterior to the cavity.

4. The method of claim 1, further comprising coating the fixation component with an agent.

5. The method of claim 1, wherein introducing the bag structure into the cavity is selected from the group consisting of introducing the bag structure by posterior entry, introducing the bag structure by lateral entry, introducing the bag structure by retroperitoneal entry and introducing the bag structure by anterior entry.

6. The method of claim 5, wherein introducing the bag structure by anterior entry comprises introducing a bag structure by mini-ALIF (Anterolateral interbody fusion) entry.

7. The method of claim 1, further comprising preparing vertebral endplates prior to introducing a bag structure.

8. The method of claim 1, further comprising closing the bag structure using a bag closure mechanism.

9. The method of claim 1, wherein the fixation component of the bag structure is placed in close proximity to a vertebral endplate within the cavity using a deployment device.

10. The method of claim 1, further comprising creating a flap in an annulus of the disc to generate a hinged portion of the annulus prior to removing the nucleus of the disc, wherein the flap of the annulus is capable of being substantially repositioned in its original position.

11. The method of claim 10, wherein creating a flap comprises creating a flap proportional to the size of the bag or implant structure when the bag or implant structure is in a delivery conformation.

12. The method of claim 1, further comprising delivering to the cavity or prosthetic device a therapeutic agent for dispersion in the cavity.

13. The method of claim 12, wherein delivering a therapeutic agent for dispersion is selected from the group consisting of delivering a biological agent, delivering a pharmaceutical agent, delivering a cellular component, delivering a molecular agent and combination thereof.

14. The method of claim 1, further comprising distracting the spine in the subject prior to implanting a prosthetic structure.

15. The method of claim 1, further comprising sizing the implant to fit the cavity.

* * * * *